(12) United States Patent
Hanselmann et al.

(10) Patent No.: US 11,600,944 B2
(45) Date of Patent: Mar. 7, 2023

(54) ELECTRICAL FEEDTHROUGH AND MEDICAL DEVICE

(71) Applicant: Scholly Fiberoptic GmbH, Denzlingen (DE)

(72) Inventors: Andreas Hanselmann, Freiburg (DE); Steffen Paul, Freiburg (DE); Maximilian Gotz, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 656 days.

(21) Appl. No.: 16/659,644

(22) Filed: Oct. 22, 2019

(65) Prior Publication Data

US 2020/0144764 A1 May 7, 2020

(30) Foreign Application Priority Data

Oct. 23, 2018 (DE) .......................... 102018126389.9

(51) Int. Cl.
*H01R 13/52* (2006.01)
*A61B 1/00* (2006.01)
(Continued)

(52) U.S. Cl.
CPC ..... *H01R 13/5224* (2013.01); *A61B 1/00124* (2013.01); *A61B 1/05* (2013.01);
(Continued)

(58) Field of Classification Search
CPC .. H01R 13/5224; H01R 13/04; H01R 13/405; H01R 13/6592; H01R 12/592; H01R 4/02; H01R 2201/12; H05K 1/0201; H05K 2201/066; H05K 2201/0189; A61B 1/00124; A61B 1/05
(Continued)

(56) References Cited

U.S. PATENT DOCUMENTS 5,798,476 A * 8/1998 Bailey .................... F42B 3/103
102/202.7
7,182,640 B2 * 2/2007 Garrett ................... H01R 31/06
29/842
(Continued)

FOREIGN PATENT DOCUMENTS

CN 101102714 A * 1/2008 ........... A61B 1/0011
CN 100411267 C * 8/2008 ........... H01R 13/521
(Continued)

*Primary Examiner* — Peter G Leigh
(74) *Attorney, Agent, or Firm* — Volpe Koenig

(57) ABSTRACT

An electrical feedthrough (1) is provided for improving the thermal properties and the electromagnetic compatibility (EMC) and also for simplified production of a medical instrument (7), in which electrical feedthrough individual contact pins (4), which are guided through a glass body (2) in a housing (20) of the instrument (7), are electrically connected to one another by a pluggable plug element (5), preferably in the form of a sheet metal part. Here, the plug element (5) firstly provides high thermal and electrical conductivity and secondly provides a shielding area that effectively prevents the input coupling of electromagnetic radiation. Preferably, the plug element (5) is formed in such a way that it independently develops a holding force for securing itself to the contact pins (4).

24 Claims, 2 Drawing Sheets

(51) Int. Cl.
*A61B 1/05* (2006.01)
*H01R 4/02* (2006.01)
*H01R 12/59* (2011.01)
*H01R 13/04* (2006.01)
*H01R 13/405* (2006.01)
*H01R 13/6592* (2011.01)
*H05K 1/02* (2006.01)

(52) U.S. Cl.
CPC ............ *H01R 4/02* (2013.01); *H01R 12/592* (2013.01); *H01R 13/04* (2013.01); *H01R 13/405* (2013.01); *H01R 13/6592* (2013.01); *H05K 1/0201* (2013.01); *H01R 2201/12* (2013.01); *H05K 2201/066* (2013.01); *H05K 2201/10189* (2013.01)

(58) Field of Classification Search
USPC ........................................................ 600/109
See application file for complete search history.

(56) References Cited

U.S. PATENT DOCUMENTS

| | | | | |
|---|---|---|---|---|
| 7,745,725 | B2 * | 6/2010 | Paterek | H01R 9/16 |
| | | | | 439/926 |
| 7,866,263 | B2 * | 1/2011 | Magne | F42B 3/103 |
| | | | | 102/202.1 |
| 8,126,556 | B2 * | 2/2012 | Hjelm | A61N 1/37 |
| | | | | 607/36 |
| 8,593,816 | B2 * | 11/2013 | Iyer | A61N 1/3754 |
| | | | | 361/728 |
| 8,921,700 | B2 * | 12/2014 | VandenEynden | H01B 17/30 |
| | | | | 174/262 |
| 9,119,970 | B2 * | 9/2015 | Van Funderburk | B23K 1/0008 |
| 9,979,118 | B2 * | 5/2018 | Khadkikar | F04B 39/121 |
| 10,483,708 | B2 | 11/2019 | Kubon et al. | |
| 2009/0044715 | A1 * | 2/2009 | Hartl | F42B 3/103 |
| | | | | 102/202.9 |
| 2012/0203292 | A1 * | 8/2012 | Deininger | A61N 1/375 |
| | | | | 607/2 |
| 2012/0203314 | A1 * | 8/2012 | Deininger | A61N 1/3758 |
| | | | | 607/115 |
| 2014/0120763 | A1 * | 5/2014 | Itsuki | H01R 13/533 |
| | | | | 439/382 |
| 2014/0166357 | A1 * | 6/2014 | Kato | H02G 3/22 |
| | | | | 174/650 |
| 2014/0168917 | A1 * | 6/2014 | Marzano | H01G 2/02 |
| | | | | 361/752 |
| 2016/0271401 | A1 * | 9/2016 | Klenner | A61N 1/37229 |
| 2017/0087358 | A9 * | 3/2017 | Deininger | A61N 1/086 |
| 2017/0188795 | A1 * | 7/2017 | Ouyang | G02B 23/2484 |

FOREIGN PATENT DOCUMENTS

| | | | | |
|---|---|---|---|---|
| DE | 102016119861 | A1 * | 4/2018 | |
| DE | 102017119691 | | 2/2019 | |
| EP | 779492 | A2 * | 6/1997 | ............. F42B 3/185 |
| EP | 2012082 | A2 * | 1/2009 | ............. F42B 3/103 |
| EP | 3069753 | A1 * | 9/2016 | ......... A61N 1/37229 |
| EP | 3163690 | A1 * | 5/2017 | ............. H01R 13/18 |
| WO | WO-2007054530 | A1 * | 5/2007 | ............. F42B 3/103 |
| WO | WO-2012102971 | A1 * | 8/2012 | ............. A61N 1/375 |

* cited by examiner

ELECTRICAL FEEDTHROUGH AND MEDICAL DEVICE

INCORPORATION BY REFERENCE

The following documents are incorporated herein by reference as if fully set forth: German Patent Application No. 10 2018 126 389.9, filed Oct. 23, 2018.

BACKGROUND

The invention relates to an electrical feedthrough for a medical device, more particularly a medical instrument, comprising a sealing glass body and an arrangement of electrical contact pins that are molded into the glass body and penetrate through the glass body. Here, the contact pins can protrude from the glass body on the inner and/or outer side while the glass body typically seals, more particularly hermetically seals, the interior of the device/instrument.

The invention further relates to a medical device, more particularly a medical instrument or endoscope or camera head, with a hermetically sealed interior comprising a heat source.

Electrical feedthroughs as described above are known and are used, for example, to create a seal in medical instruments and for devices as described above, said seal allows, firstly, hermetic sealing of the interior and, at the same time, reliable electrical contacting of electronics in the interior and, secondly, withstanding of a typical temperature load during autoclaving, as required for medical devices. A further requirement of such applications lies in the electromagnetic compatibility (EMC), which requires appropriate shielding of electronic components within the device.

SUMMARY

The invention is based on the object of creating an electrical feedthrough with improved use properties.

In order to achieve this object, one or more features according to the invention are provided in an electrical feedthrough. In particular, what is consequently provided according to the invention for the purposes of achieving the object in the case of an electrical feedthrough of the type set forth at the outset is that a metallic plug element is plugged onto at least two of the contact pins, which protrude from the glass body on the inner and/or outer side, and cohesively connected to the at least two contact pins such that the at least two contact pins are electrically connected to one another. Here, the cohesive connection can preferably be brought about by soldering.

An advantage of such a configuration is that an excellent thermal connection can be established between the two contact pins by the choice of a metallic plug element that is in contact with, preferably areal contact with, the at least two contact pins. As will still be explained in more detail below, this can particularly efficiently dissipate heat losses from an interior of the device to the outside. Moreover, such a plug element significantly improves the EMC of the device, to be precise in particular when the plug element is electrically connected to an electrical shield of the connecting cable of the device.

Here, the plug element can be plugged onto respective contact pins on both the inner side and the outer side—in relation to the installed position of the feedthrough. Consequently, the electrical feedthrough may also comprise a plurality of plug elements, which are plugged onto two contact pins of the arrangement in each case, on the inner and/or outer side, and which are cohesively connected to the respective contact pins.

Here, contact pins can be understood to mean electrical connector pins that allow electrical power and/or signals to be transferred through the glass body. The contact pins can preferably be formed from a metal that has excellent electrical conductivity and that is corrosion resistant and, moreover, said contact pins may have coatings that facilitate improved soldering.

Further advantageous configurations that serve to achieve the object set forth at the outset are described below and in the claims.

Thus, the plug element can preferably have an elastic embodiment, for example by appropriate forming. As a result, the plug element can exert a pretension on the at least two contact pins after being plugged onto the at least two contact pins. This is very advantageous, in particular for a simple assembly and for simplifying the soldering of the plug element on the contact pins.

Further, the plug element can protrude beyond the at least two contact pins in the axial and/or radial direction. While an axial protrusion is advantageous for simple electrical contacting of the plug element, the radial protrusion ensures that efficient shielding is obtained.

In one advantageous configuration, provision can be made for the plug element, respectively along a circumferential portion, to abut against each of the at least two contact pins. By way of example, this can achieve areal contacting, particularly if the cohesive connection extends over this circumferential portion.

The plug element may have two opposing side faces, particularly in the case of a band-shaped configuration. In this case, it is particularly expedient for each of the opposing side faces of the plug element to abut against at least one contact pin of the arrangement in each case, but preferably against at least two contact pins of the arrangement in each case. In particular, this abutment can result in an areal contact. What is consequently achievable is that the plug element can be clamped between the contact pins.

It is particularly preferred for the plug element to be in contact with at least three contact pins along a respective circumferential portion, the contact pins being alternately arranged on opposing side faces along an extent of the plug element.

So as to further improve the electromagnetic shield, provision can further be made for the plug element to be connected to a shield of an electrical connecting cable. Further, the plug element may provide a shielding face that covers the at least two contact pins.

Further, particularly good shielding can be obtained if the at least two contact pins, onto which the plug element is plugged, are placed on outer positions of the arrangement. This is because the plug element can shield the arrangement to the outside in this case. Here, it may be advantageous if the at least two contact pins are embodied with a larger cross section than that of a cross section of contact pins of the arrangement on inner positions, more particularly a cross section that is more than twice as large.

This is because, firstly, this allows a large number of contact pins to be housed in a tight space. Secondly, a large cross section of the at least two contact pins is advantageous for establishing a reliable cohesive connection to the plug element and for ensuring sufficient mechanical stability of the entire arrangement.

According to a preferred configuration, provision is made for a metallic plug element to be plugged onto at least two contact pins of the arrangement, protruding from the glass body in each case, on each of the two sides of the glass body, said metallic plug elements preferably being identical and said metallic plug elements being connected to the respective at least two contact pins. Here, the connection between the respective plug element and the respective contact pins can be implemented in cohesive fashion, for example by soldering, or else by a force fit. Such connections are advantageous both in view of EMC and also in view of the dissipation of heat. Here, provision can be made for at least two contact pins to each occupy outer positions within the arrangement on the inner and outer side of the feedthrough.

In order to open up medical applications, the feedthrough can have a treatable, more particularly autoclavable, configuration.

A further preferred configuration provides for the plug element to have openings such that contact pins situated behind the plug element are accessible from the outside. Consequently, solder can be guided from radially on the outside to the contact pins situated directly behind the plug element through the opening in the plug element in the plugged state in order thus to be able to solder the plug element to these contact pins.

Preferably, the plug elements can be applied to the contact pins in such a way here that lateral free regions remain between the plug elements. These lateral free regions allow inner contact pins of the arrangement to remain accessible from the outside through the free regions, said inner contact pins of the arrangement being able to have a thinner embodiment than the outer contact pins, in particular. As a result, the inner contact pins can be soldered to connecting cables, to be precise even after the plug elements have been soldered onto the outer contact pins. Consequently, a simple assembly of the feedthrough can be ensured, despite shielding by the plug element or elements.

The plug element itself preferably has a band-shaped form and/or is formed as a bent-up part made of sheet metal. Further, it can abut against the arrangement in interlocking fashion and/or be secured to the arrangement in interlocking fashion. In certain embodiments, at least two of the contact pins of the arrangement can be guided through the plug element.

Further, the plug element may have a profile that, at least in portions, engages around the at least two contact pins at outer positions of the arrangement in radial fashion on the inner and/or outer side. Here, it is preferable for the profile to engage around two further contact pins at outer positions of the arrangement only radially on the outside or else only radially on the inner side, to be precise, in particular, in such a way that the profile exerts a securing force on the contact pins on account of an elastic deformation.

Additionally, the plug element can also be aligned in longitudinal fashion in relation to the contact pins, i.e., in particular, abut against the length of the contact pins with an areal lower or upper side.

As mentioned previously, openings may be provided in the plug element, said openings facilitating soldering of the contact pins themselves on the plug element and the soldering of inner contact pins on, e.g., connection slots of the previously mentioned connecting cable after the plug element has been plugged onto the contact pins. Additionally, or as an alternative thereto, the plug element may also, however, have push-through openings for receiving individual contact pins of the arrangement.

The plug element can be secured particularly reliably on the contact pins when the plug element contacts at least two, but preferably at least three, of the at least two contact pins, at least along a respective circumferential portion. In particular, this contacting can be implemented by different side faces of the plug element. By way of example, the plug element can contact at least one contact pin, but preferably two contact pins, with its lower side and can contact at least one contact pin with its upper side, or precisely the other way around. This is particularly expedient if the plug element has a band-shaped configuration, i.e., preferably has a configuration that is wider and longer than thick. In order to prevent slippage of the plug element still prior to the soldering, the circumferential portion preferably encompasses at least 30°.

To achieve the aforementioned object, an electrical feedthrough having one or more features of the invention is also provided. In particular, according to the invention, an alternative solution to the aforementioned object is consequently proposed in the case of an electrical feedthrough of the type set forth at the outset, according to which alternative solution a heatsink is electrically connected to at least one of the contact pins on a side of the glass body that lies on the inside in the installed position. Consequently, particularly efficient heat transport can be ensured within an interior of the device to the feedthrough and through the feedthrough to the outside such that, in particular, it is possible to meet critical technical specifications for medical products. All of the features of the electrical feedthrough mentioned above may also be realized in such a configuration.

An electrical contact between the heatsink and the at least one contact pin can be realized, in particular, by the use of a metallic plug element, more particularly as described above. Here, this plug element can thus be plugged on the inner side onto at least two contact pins of the arrangement and can be cohesively connected, i.e., soldered, in particular, to these two contact pins.

According to further advantageous configuration, individual contact pins can be electrically connected to a printed circuit board lying on the inside in an installed position. This allows, firstly, the printed circuit board to be supplied with voltage and current and, secondly, signals from the printed circuit board to be guided to the outside. Here, it is preferable for a ground connector of the printed circuit board to be guided to the outside by one of the contact pins of the arrangement, wherein this contact pin is electrically connected to a, or the, plug element on the outer side and/or can be arranged at an outer position of the arrangement.

The heatsink, in turn, can receive the printed circuit board within itself. To this end, the heatsink can have a multipart embodiment, for example an embodiment in two parts, wherein each of the parts can be electrically connected to one of the contact pins, preferably by a plug element. Here, it is particularly preferable for the parts of the heatsink to be electrically and thermally connected to one another, preferably by way of metallic contacts.

Further, the two part or multipart heatsink can be enveloped by a shield, for example by virtue of a copper band being wound there-around. This can obtain electromagnetic shielding.

A preferred structure provides for the heatsink to be held by an electrically insulating frame, wherein the frame may alternatively, or else in complementary fashion, be electrically insulated from the heatsink, for example by a coating.

In order to facilitate particularly high heat dissipation, the heatsink can be in electrical and/or thermal contact with the printed circuit board by way of contact areas formed on the printed circuit board. In turn, the heatsink may have a thermal contact area which is at least thermally coupled to an electronic component of the printed circuit board in order to dissipate heat that arises in the component.

Further, a medical device, more particularly a medical instrument or endoscope or camera head, is proposed for the purposes of achieving the object set forth at the outset. The device, which comprises a hermetically sealed interior comprising a heat source, is now characterized in that electrical contacts are guided from the interior to the outside by an electrical feedthrough as described herein and/or as claimed in any one of the claims directed to an electrical feedthrough.

Here, in particular, the aforementioned heatsink and the printed circuit board can be arranged in the interior. Furthermore, the heat source can be, e.g., an FPGA, preferably an image-preparing FPGA. Hence, in particular, a configuration of a camera head or of an endoscope is described, which supplies excellent signal quality on account of the vicinity of the electronics to the image sensor and which, furthermore, is well shielded from an electrical point of view and moreover does not lead to any impermissible heating of human tissue when the endoscope or camera head is used inside the human body during surgical interventions.

BRIEF DESCRIPTION OF THE DRAWINGS

The invention will now be described in more detail on the basis of exemplary embodiments, although it is not restricted to these exemplary embodiments. Further exemplary embodiments arise by combining the features of individual claims or of a plurality of claims among themselves and/or with individual features or a plurality of features of the respective exemplary embodiment. In particular, it is consequently possible to obtain embodiments of the invention from the following description of a preferred exemplary embodiment in conjunction with the general description, the claims and the drawings.

In detail:

FIG. 14 shows a plug element according to the invention, after three contact pins have been plugged on.

DETAILED DESCRIPTION

Figure 1:
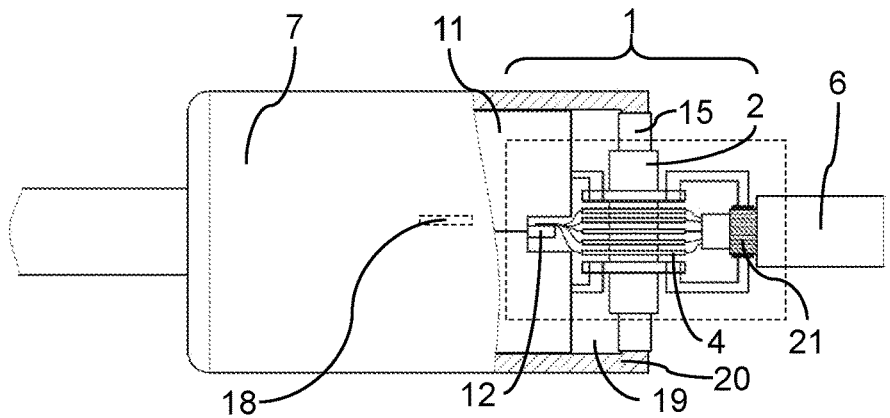
FIG. 1 shows a schematic side view with a partial longitudinal section through an instrument according to the invention, which comprises an electrical feedthrough configured according to the invention.

In the following description of various embodiments of the invention, elements that correspond in terms of their function are provided with corresponding reference numerals, even in the case of a deviating design or shape.

FIG. 1 shows an electrical feedthrough, denoted by 1 overall, which is used to electrically connect a printed circuit board 12 in an interior 19 of a medical instrument 7 to a connecting cable 6. Consequently, the feedthrough 1 serves to guide electrical contacts 23 on the printed circuit board 12 from the interior 19 to the outside. To this end, the feedthrough 1 comprises a symmetric arrangement 3 of contact pins 4, wherein individual contact pins 4 are connected to the printed circuit board 12 on the inside and to respective connection slots of the connecting cable 6 on the outside.

The contact pins 4 are molded with a set arrangement 3 into a glass body 2 which, in turn, is inserted in hermetically sealed fashion into a mount 15 of a housing 20 of the instrument 7. As can easily be identified on the basis of FIG. 2, all contact pins 4 of the arrangement 3 protrude from the glass body 2 on both the inner side and the outer side, with the contact pins 4 having an embodiment with a uniform length and protruding on both sides of the glass body 2 with a uniform length.

As is evident from the overview of FIGS. 1 to 4, a metallic plug element 5 in the form of a bent sheet of metal is plugged onto two of the contact pins 4 of the arrangement on the outer side of the glass body 2. In order to cohesively connect the plug element 5 to the two contact pins 4 (arranged right at the top in FIG. 3), the plug element 5 has been soldered to these two contact pins 4 after having been plugged on. To this end, an opening 9 is provided in each case (see FIG. 4) such that solder can be guided from the outside to the respective contact pin 4 through the opening 9. Consequently, the openings 9 serve to solder the contact pins 4 to the plug element 5, wherein damage to the thinner, interior contact pins 4 of the arrangement 3 can be avoided during soldering as a result of the access from the outside. The thinner, interior contact pins 4 of the arrangement 3 are in turn accessible by way of the lateral free regions between the plug elements 5.

Additionally, a second plug element 5 with the same design is provided on the outer side, said second plug element being plugged in a manner analogous to the first upper plug element 5 onto two contact pins 4 on outer positions of the arrangement 3 and being soldered to the latter. Here, the second plug element 5 and the first plug element 5 are arranged in symmetric fashion in relation to the arrangement 3.

Figure 4:
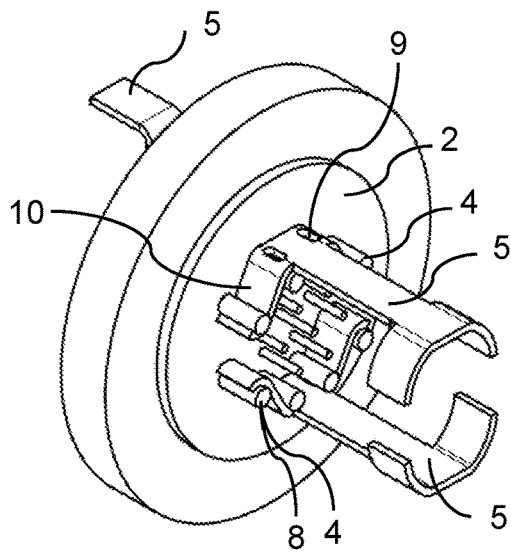
FIG. 4 shows a view of the outer side of the glass body of FIG. 3 after plugging-on the plug elements.

As shown in FIG. 4, each of the two outer plug elements 5 protrudes beyond the contact pins in the axial direction. Here, the respective ends of the two plug elements 5 on the outer side are respectively electrically connected to a shield 21 of the connecting cable 6, as a result of which excellent shielding emerges. As a result of the two plug elements 5 respectively abutting against the outer side of the respective contact pins 4, said plug elements also protrude beyond the latter in the radial direction.

It is at least easily conceivable on the basis of FIG. 4 that the plug element 5 is so elastic that it exerts a pretension on the contacted contact pins 4 in the plugged position. As a result, a holding force arises, and so the plug element can be secured to the arrangement in self-supporting fashion even before soldering. To this end, the plug element 5 shown in FIG. 4 has an elastic wing at its two ends, said elastic wing being deflectable counter to a restoring force. Consequently, the form of the plug element 5 in the plugged position, as shown in FIG. 4, deviates from a form at rest, which the plug element 5 has when no external forces act.

Here, the elasticity of the plug element 5 is substantially based on its band form. It can easily be identified in FIG. 4, in particular, that the plug element is longer and wider than the material thickness of the sheet metal from which it is manufactured.

As may be identified on the basis of FIG. 4, the upper plug element 5 is plugged onto a total of four contact pins 4 on the outer side, said four contact pins all having an embodiment with a larger cross section than the seven contact pins 4 that are arranged in the interior of the arrangement 3 (see FIG. 3); here, the cross section of the eight outer contact pins 4 of the arrangement 3 is more than twice the cross section of the seven interior contact pins 4 of the arrangement 3.

As can be seen in FIG. 4, the outer upper plug element 5 abuts radially to the outside against two of the four contact pins 4 while it abuts radially on the inside against the two remaining contact pins 4 of said four contact pins. Here, the radius corresponds to that of the glass body 2 with a circular disk shape. On account of the shape of the plug element 5, there moreover is an interlocking connection with a respective circumferential portion of the respective contact pin 4.

The profile 10 of the plug element 5 further ensures that the plug element 5, as may easily be identified in FIG. 4, engages around the two inner contact pins of the four contact pins 4 radially on the outside and engages around the two outer contact pins of the four contact pins 4 radially on the inside.

Figure 6:
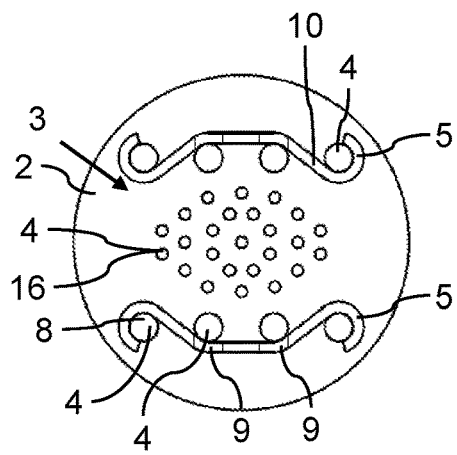
FIG. 6 shows a frontal view of an electrical feedthrough according to the invention with two plugged-on plug elements.
Figure 7:
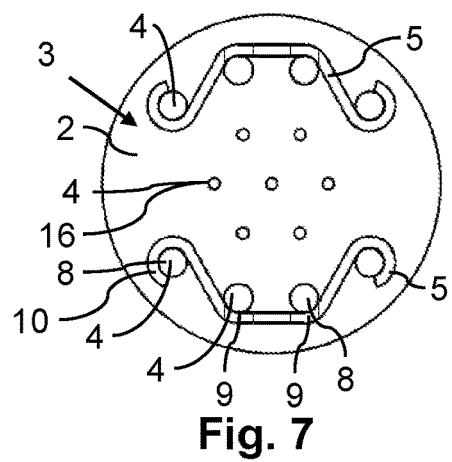
FIG. 7 shows a frontal view of a further electrical feedthrough according to the invention with two plugged-on plug elements.

Further possible configurations of feedthroughs 1 according to the invention are shown in FIGS. 6 and 7. Here, too, eight contact pins 4 are respectively arranged on outer positions of the arrangement 3 while a multiplicity of contact pins 4 with comparatively smaller cross section are arranged in the center of the arrangement 3 in each case.

Figure 8:
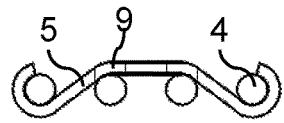
FIGS. 8 to 10, and 12 show frontal views of contact pins highlighting different options for plugging plug elements according to the invention onto contact pins.
Figure 9:
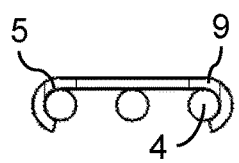
Figure 10:
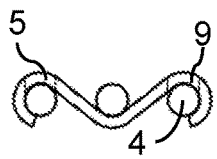
Figure 11:
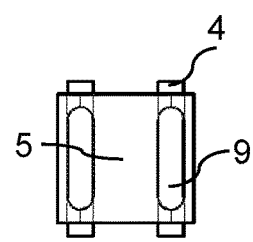
FIG. 11 shows a plan view of a plug element according to the invention which is plugged onto two contact pins.
Figure 12:
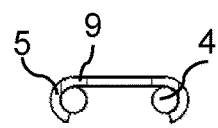

In the two configurations of the plug element 5 shown in FIGS. 6 and 7, said plug element in each case engages around two contact pins 4 at outer positions only on the outer side, while the plug element 5 in each case engages around two further contact pins 4 at outer positions, specifically the two contact pins 4 that are encompassed by the respective ends of the plug element 5, both radially on the inside and radially on the outside. Such configurations result in particularly reliable securing of the plug element 5 at the respective contact pins 4. FIGS. 8 to 10 also show such forms of plug elements 5, while FIG. 12 shows a simpler variant in which the plug element 5 only engages around two contact pins 4.

It is evident from the exemplary embodiments according to FIG. 6 and FIG. 7 that the plug element 5 in each case contacts the contact pins 4 along a circumferential portion. The cohesive connection is formed in these circumferential portions. It is evident that two of the contact pins 4, for example the outer two contact pins, abut against one side face of the band-shaped plug element 5 while the other two contact pins 4, more particularly the inner or inner-lying contact pins 4, abut against the opposite side face of the plug element 5.

It is further possible to identify from FIG. 6 that the upper and the lower plug element 5 each contact four contact pins 4, in each case along a respective circumferential portion. For the two contact pins 4 arranged on the inside in relation to the ends of the plug element 5, said circumferential portion is approximately 20° while the contacted circumferential portion is more than 180° for the two contact pins 4 around which the ends of the plug element 5 engage.

Figure 13:
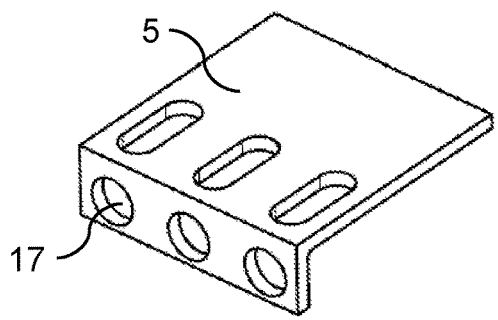
FIG. 13 shows a plug element according to the invention.
Figure 14:
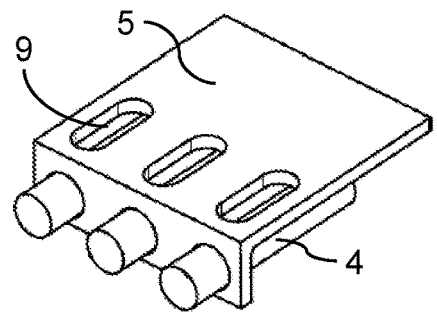

FIG. 13 illustrates a further possible configuration of a plug element 5 according to the invention with push-through openings 17 which, as shown in FIG. 14, are provided to receive contact pins 4 of the feedthrough 1. Consequently, the plug element is plugged onto the contact pins 4 by being pushed on same in such a configuration.

Figure 5:
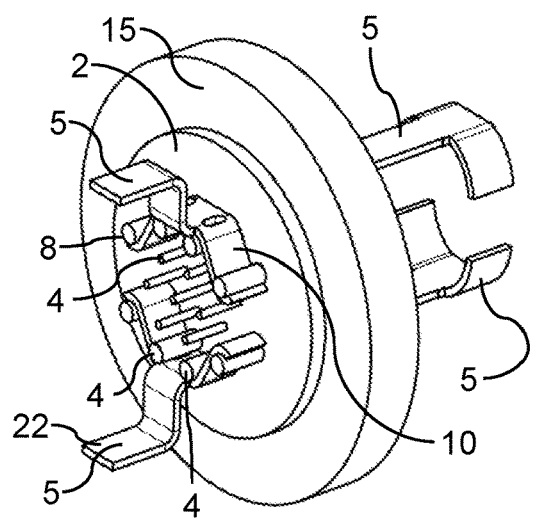
FIG. 5 shows the electrical feedthrough of FIG. 4, albeit as viewed from the inner side of the glass body.

As shown in FIG. 5, the feedthrough 1 comprises two further inner plug elements 5, which are embodied in identical fashion among themselves, but which differ in terms of their form from the two outer plug elements 5. However, the inner plug elements 5 are also axially plugged onto at least 2 contact pins and soldered to the latter.

It is further possible to identify that the two inner and the two outer plug elements 5 are each plugged onto identical contact pins 4 of the arrangement 3 such that a corresponding arrangement arises between the inner side and the outer side of the feedthrough 1. Expressed differently, respectively one outer plug element 5 is consequently electrically short-circuited with a corresponding inner plug element 5 by way of respective contact pins 4.

By way of example, if the respective longitudinal form of the plug elements 5 is followed in FIG. 5, it is possible to identify that each individual one of the four plug elements 5 of the feedthrough 1 is aligned in the longitudinal direction of the contact pins 4.

FIG. 1 also illustrates a heatsink 11. The latter is electrically connected, and hence also thermally connected, to one of the contact pins 4 of the feedthrough 1 by an inner plug element 5. As may be identified from FIG. 2, the heatsink 11 is consequently also thermally connected to an outer plug element 5.

As a result of these two upper plug elements 5 (in FIG. 2) being connected to a plurality of contact pins 4, it becomes possible to efficiently transport heat to the outside through the feedthrough 1, said heat being produced by an FPGA as a heat source 18 on the printed circuit board 12 and being taken up by the heatsink 11. To this end, the inner plug elements 5 have contacting points 22 with an areal embodiment, which facilitate good thermal coupling to the heatsink 11.

Figure 2:
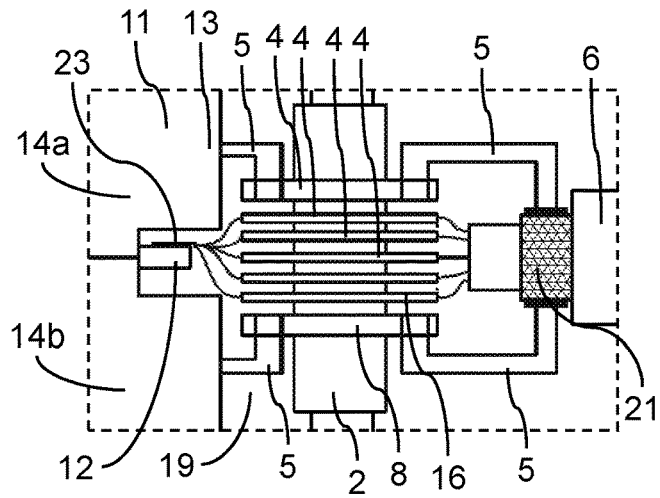
FIG. 2 shows a detailed view (dashed in FIG. 1) of the feedthrough of FIG. 1.
Figure 3:
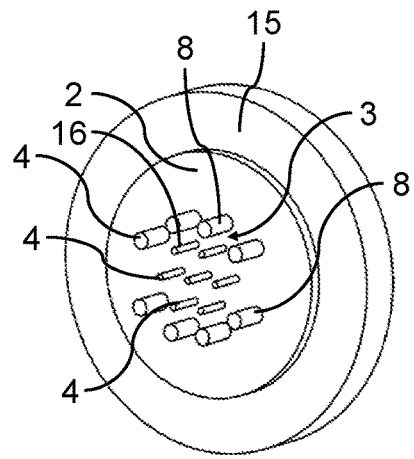
FIG. 3 shows a realistic perspective view of the outer side of the glass body with inserted contact pins of the feedthrough of FIG. 1 prior to the plugging-on of plug elements according to the invention.

Here, the heatsink 11 consists of two parts 14a and 14b, wherein the printed circuit board 12, as may be identified in the detailed view of FIG. 2, is placed between the two parts such that the heatsink 11 receives the printed circuit board 12 within itself and therefore takes up heat from the printed circuit board 12 from all sides. Moreover, the two parts 14a and 14b are electrically short-circuited in order thus to facilitate improved thermal conductivity, even within the heatsink 11.

By contrast, the figures do not show that the heatsink 11 has a thermal contact face that is in thermal contact with an FPGA as a heat source 18 on the printed circuit board 12 in order to be able to directly dissipate the heat arising in the FPGA with little thermal resistance.

In conclusion, an electrical feedthrough 1 is provided for improving the thermal properties and the electromagnetic compatibility (EMC) and also for simplified production of a medical instrument 7, in which electrical feedthrough individual contact pins 4, which are guided through a glass body 2 in a housing 20 of the instrument 7, are electrically connected to one another by a pluggable plug element 5, preferably in the form of a metallic sheet part. Here, the plug element 5 firstly provides high thermal and electrical conductivity and secondly provides a shielding area that effectively prevents the input coupling of electromagnetic radiation. Preferably, the plug element 5 is formed in such a way that it independently develops a holding force for securing itself to the contact pins 4.

LIST OF REFERENCE SIGNS

1 Electrical feedthrough
2 Glass body
3 Arrangement
4 Contact pin
5 Plug element
6 Connecting cable
7 Medical instrument
8 Outer position (of 3)
9 Opening (of 5)
10 Profile (of 5)
11 Heatsink
12 Printed circuit board
13 Ground connector (of 12)
14a (Upper) part (of 11)
14b (Lower) part (of 11)
15 Mount (of 2)
16 Inner position (of 3)
17 Push-through openings (for 4 in 5)
18 Heat source
19 Interior (of 7)
20 Hermetic housing (of 7)
21 Shield (of 6)
22 Contacting point (at 5 for 11)
23 Electrical contacts

The invention claimed is:

1. An electrical feedthrough (1) for a medical device, the electrical feedthrough (1) comprising:
a sealing glass body (2);
an arrangement (3) of electrical contact pins (4) molded into the glass body (2) that penetrate through the glass body (2); and
a metallic plug element (5) plugged onto at least two of the contact pins (4), which protrude from the glass body (2) on at least one of an inner or outer side thereof, the metallic plug element and the at least two of the contacts are cohesively connected to the at least two contact pins (4) such that the at least two contact pins (4) are electrically connected to one another in a completed assembly of the feedthrough.

2. The electrical feedthrough (1) as claimed in claim 1, wherein the metallic plug element and the at least two of the contacts are cohesively connected with solder.

3. The electrical feedthrough (1) as claimed in claim 1, wherein the plug element (5) is elastic and, after being plugged onto the at least two contact pins (4), exerts a pretension on the at least two contact pins (4).

4. The electrical feedthrough (1) as claimed in claim 1, wherein the plug element (5) protrudes beyond the at least two contact pins (4) in at least one of an axial or radial direction.

5. The electrical feedthrough (1) as claimed in claim 1, wherein the plug element (5), along a circumferential portion, abuts against each of the at least two contact pins (4), respectively, and the plug element (5) has two opposing side faces and each of said side faces abuts against at least one said contact pin (4).

6. The electrical feedthrough (1) as claimed in claim 1, further comprising a shield (21) of an electrical connecting cable (6), and the plug element (5) is connected to the shield (21) of an electrical connecting cable (6).

7. The electrical feedthrough (1) as claimed in claim 1, wherein the at least two of the contact pins (4) are placed on outer positions (8) of the arrangement (3), and have a cross section that is more than twice as large as that of the contact pins (4) of the arrangement (3) located at inner positions (16).

8. The electrical feedthrough (1) as claimed in claim 1, further comprising an additional metallic plug element, and one said metallic plug element (5) is plugged onto at least two contact pins (4) of the arrangement (3), protruding from the glass body (2) in each case, on each of the two sides of the glass body (2).

9. The electrical feedthrough (1) as claimed in claim 8, wherein said metallic plug elements are identical and said metallic plug elements are cohesively connected to the respective at least two of the contact pins (4).

10. The electrical feedthrough (1) as claimed in claim 1, wherein the feedthrough (1) is configured to be autoclavable.

11. The electrical feedthrough (1) as claimed in claim 1, wherein at least two of the contact pins (4) occupy outer positions (8) within the arrangement (3) on an inner and an outer side of the feedthrough (1).

12. The electrical feedthrough (1) as claimed in claim 1, wherein the plug element (5) includes openings (9) such that contact pins (4) situated behind the plug element (5) are accessible from the outside.

13. The electrical feedthrough (1) as claimed in claim 1, wherein the plug element (5) at least one of has a band-shaped form or is formed as a bent-up part made of sheet metal, and abuts against, or is secured to, the arrangement (3) in interlocking fashion, with at least two of the contact pins (4) guided through the plug element (5), and the plug element (5) has a profile (10) that, at least in portions, engages around the at least two contact pins (4) at outer positions (8) of the arrangement (3) in radial fashion on at least one of an inner or outer side.

14. The electrical feedthrough (1) as claimed in claim 13, wherein the profile engages around two further ones of the contact pins (4) at outer positions (8) of the arrangement (3) only radially on the outside or only radially on the inner side, such that the profile exerts a securing force on the contact pins (4) due to an elastic deformation of the plug element, and the plug element (5) is aligned longitudinally in relation to the contact pins (4).

15. The electrical feedthrough (1) as claimed in claim 1, wherein openings (9) are provided in the plug element (5), said openings facilitating soldering of the contact pins (4) after plugging the plug element (5) thereon same, and the plug element (5) includes push-through openings (17) for receiving individual contact pins (4).

16. The electrical feedthrough (1) as claimed in claim 1, wherein the plug element (5) contacts at least two or at least three of the at least two contact pins (4), at least along a respective circumferential portion, with different side faces of the plug element (5).

17. A medical device, comprising at least one of a medical instrument (7), an endoscope or a camera head, the medical device further comprising a hermetically sealed interior (19) including a heat source (18), electrical contacts (23) that are guided from the interior (19) to outside by an electrical feedthrough (1) as claimed in claim 1, a heatsink (11) arranged in the interior, and a printed circuit board (12) arranged in the interior (19), wherein the heat source (18) comprises an FPGA.

18. An electrical feedthrough (1) for a medical device, the electrical feedthrough (1) comprising:

a sealing glass body (2), an arrangement (3) of electrical contact pins (4) molded into the glass body (2) that penetrate through the glass body (2), a heatsink (11) electrically connected to at least one of the contact pins (4) on a side of the glass body (2) that lies on an inside in an installed position.

19. The electrical feedthrough (1) as claimed in claim 18, further comprising a metallic plug element (5) that provides an electrical contact between the heatsink (11) and the at least one contact pin (4), the metallic plug element (5) is plugged on an inner side onto two of the contact pins (4) of the arrangement (3) and cohesively connected to said two contact pins (4).

20. The electrical feedthrough (1) as claimed in claim 19, wherein individual ones of the contact pins (4) are electrically connected to a printed circuit board (12) lying on the inside in an installed position, a ground connector (13) of the printed circuit board (12) is guided outside by one of the contact pins (4) of the arrangement (3), and said contact pin (4) is electrically connected to the plug element (5) on at least one of the outer side or arranged at an outer position (8) of the arrangement (3).

21. The electrical feedthrough (1) as claimed in claim 20, wherein the heatsink (11) receives the printed circuit board (12) therein, the heatsink (11) is formed in a plurality of parts (14a, 14b) and each of the parts (14a, 14b) is electrically connected to one of the contact pins (4), by the plug element (5), and the parts (14a, 14b) of the heatsink (11) are at least one of electrically or thermally connected to one another, or wherein the heatsink (11) is enveloped by a shield.

22. The electrical feedthrough (1) as claimed in claim 20, further comprising an electrically insulating frame that holds the heatsink (11) or wherein the heatsink (11) is in at least one of electrical or thermal contact with the printed circuit board (12) by contact areas formed on the printed circuit board (12).

23. The electrical feedthrough (1) as claimed in claim 20, wherein the heatsink (11) has a thermal contact area which is in thermal contact with an electronic component of the printed circuit board (12) that is adapted to dissipate heat that arises in the component.

24. A medical device, comprising at least one of a medical instrument (7), an endoscope or a camera head, the medical device further comprising a hermetically sealed interior (19) including a heat source (18), electrical contacts (23) that are guided from the interior (19) to outside by an electrical feedthrough (1) as claimed in claim 18, and a printed circuit board (12) arranged in the interior (19), wherein the heat source (18) comprises an FPGA.

* * * * *